United States Patent [19]

Davis et al.

[11] Patent Number: 4,994,427

[45] Date of Patent: Feb. 19, 1991

[54] SUPPORTED AQUEOUS PHASE ORGANOMETALLIC CATALYST USEFUL FOR HYDROFORMYLATION AND OTHER REACTIONS, AND A METHOD FOR ITS PREPARATION

[75] Inventors: Mark E. Davis; Juan P. Arhancet; Brian E. Hanson, all of Blacksburg, Va.

[73] Assignee: Virginia Tech Intellectual Properties, Inc., Blacksburg, Va.

[21] Appl. No.: 276,825

[22] Filed: Nov. 28, 1988

[51] Int. Cl.$^5$ .............................................. B01J 31/22
[52] U.S. Cl. .................................. 502/166; 502/161; 502/150; 502/164
[58] Field of Search ................. 502/161, 166, 150, 164

[56] References Cited

U.S. PATENT DOCUMENTS

| | | | |
|---|---|---|---|
| Re. 31,812 | 1/1985 | Kuntz | 502/166 X |
| 3,855,307 | 12/1974 | Rony et al. | 502/166 X |
| 4,157,313 | 6/1979 | Conan et al. | 568/454 |
| 4,193,942 | 3/1980 | Gerritsen et al. | 502/166 X |
| 4,334,101 | 6/1982 | Mantovani et al. | 568/454 |
| 4,348,539 | 9/1982 | Billig et al. | 568/454 |
| 4,356,125 | 10/1982 | de Munck et al. | 568/454 |
| 4,504,684 | 3/1985 | Fox et al. | 568/454 |

FOREIGN PATENT DOCUMENTS 1185453  3/1970  United Kingdom .

OTHER PUBLICATIONS

A. F. Borowski et al, "Water-Soluble Transition Metal Phosphine Complexes . . . ", Nouveau Jousnal De Chemie, vol. 2, No. 2, p. 137-144.
L. A. Gerritsen et al, "Hydroformylation With Supported Liquid Phase Rhodium Catalysts, Part I" J. Molecular Catalysis, 9 (1980) 139-155.
L. A. Gerritsen et al, "Hydroformulation With Supported Liquid Phase Rhodium Catalysts, Part II" J. Molecular Catalysis, 9 (1980) 157-168.
L. A. Gerritsen et al, "Hydroformylation With Supported Liquid Phase Rhodium Catalysts, Part 3" J. Molecular Catalysis, 9 (1980) 241-256.
L. A. Gerritsen et al, "Hydroformylation With Supported Liquid Phase Rhodium Catalysts, Part IV" J. Molecular Catalysis, 9 (1980) 257-264.
L. A. Gerritsen et al, "Hydroformylation With Supported Liquid Phase Rhodium Catalysts, Part V" J. Molecular Catalysis, 9 (1980) 265-274.
N. A. de Munck et al, "Gas Phase Hydrofromylation of Alkyl Alcohol With Supported Liquid Phase Rhodium Catalysts," J. Molecular Catalysis, 11 (1981) 233-246.
H. L. Pelt et al, "Hydroformylation of Alkenes With Supported Liquid Phase Rhodium Catalysts . . . ", J. Molecular Catalysis, 31 (1985) 107-118.
H. L. Pelt et al, "Hydroformylation of Butene-1 and Butene-2 Over Rhodium-SLP Catalysts . . . " J. Molecular Catalysis, 31 (1985) 371-383.
H. L. Pelt et al, "The Thermal and Chemical stbaility Limits of Supported Liquid Phase Rhodium Catalysts in the Hydroformylation of Propene," J. Molecular Catalysis, 33 (1985) 119-128.

Primary Examiner—Patrick P. Garvin

[57] ABSTRACT

This invention relates to a catalyst comprising a solid surface having immobilized thereon an aqueous solution of one or more organic complexes of rhodium. The catalyst is useful for promoting hydroformylation, hydrogenation and other chemical reactions in essentially water-immiscible organic liquid reactant phases.

24 Claims, No Drawings

SUPPORTED AQUEOUS PHASE ORGANOMETALLIC CATALYST USEFUL FOR HYDROFORMYLATION AND OTHER REACTIONS, AND A METHOD FOR ITS PREPARATION

This invention relates to a catalyst system useful for promoting a variety of chemical reactions. More particularly, this invention relates to a catalyst system comprising an aqueous phase organometallic complex, most particularly a rhodium complex, immobilized on a solid surface. This catalyst is useful for promoting reactions in essentially water-immiscible organic liquids. The invention further relates to a method for the preparation of such catalysts.

BACKGROUND OF THE INVENTION

Organometallic complexes, particularly complexes of rhodium, are well known to catalyze a variety of useful organic reactions, including for instance, hydrogenation, oxidation and carbonylation of olefinic reactants in connection with the synthesis of pharmaceuticals, dyes, insecticides, solvents, detergents, and other valuable products.

In conventional practice, catalytically active rhodium complexes have principally been applied in homogeneous form, in solution in an organic reactant phase. As such, their use has suffered from the difficulties inherent in the recovery of homogeneous catalysts from the reaction products. Effective catalyst recovery has often been a necessity when applying such complexes, because of the value of the complexes and/or because of the requirements for product purity.

As described in U.S. Pat. No. 4,248,802, it is also known that aqueous solutions of rhodium complexes can be applied to catalyze conversions of water-immiscible reactants. However, such immiscible aqueous catalyst solutions have generally exhibited low activity, possibly attributable to the low interfacial area between aqueous and organic phases.

Several catalysts have been reported which support an organometallic complex on a solid surface in the form of a liquid solution in a (nonaqueous) solvent. In conventional practice, such catalyst systems have been applied to promote vapor phase reactions. Condensation of reaction products from the vapor phase onto the surface of the liquid catalyst phase has proven to be troublesome. In cases in which the catalyst support material is a porous solid, product condensation can result in blockage of the pore void spaces. Attempts to solve the problems caused by condensation have generally centered upon increasing the temperatures at which the catalyst is applied, although this in turn has led to loss of catalyst components (e.g., solvents and ligands) through evaporation from the supported liquid phase and to degradation and deactivation of the organometallic complex.

The principal object of this invention is a heterogeneous catalyst system suitable for application in liquid reaction mixtures, which comprises an organometallic complex of rhodium immobilized in a catalytically-active, essentially non-leaching form on a solid surface.

SUMMARY OF THE INVENTION

The present invention provides a supported liquid phase catalyst wherein the liquid phase comprises a solution of a rhodium complex in water. This liquid phase is immobilized on the surface of a solid, preferably a porous solid. The catalyst of the invention is particularly useful for promoting liquid phase reactions, wherein the liquid reactant (and product) phase is essentially water-immiscible.

The immobilized aqueous solution of the catalyst system of the invention effectively binds the organometallic complex and prevents significant loss (e.g., by leaching) into essentially water-immiscible liquid reaction mixtures. In preferred embodiments, the aqueous solution is immobilized in the form of a film on the external and pore surfaces of a porous solid, providing a large interfacial area for contact between the catalytically active aqueous liquid solution and an organic liquid reactant phase.

Accordingly, in this respect, the invention is described in summary as a catalyst comprising a solid surface having immobilized thereon an aqueous solution of one or more complexes of rhodium.

In another respect, the invention is a process for the preparation of preferred embodiments of such supported aqueous phase catalysts, which comprises steps for impregnating the external and pore surfaces of a porous solid catalyst support with a solution of at least one water soluble rhodium complex in a volatile solvent, evaporating said solvent from the impregnated catalyst, and condensing water vapor on the surfaces of the solid to form on said surfaces a film of an aqueous solution of the complex.

DETAILED DESCRIPTION OF THE INVENTION

Catalysts of the invention comprise an aqueous solution of a water-soluble organometallic complex, immobilized on a solid surface. As used herein, the term "complex" is understood to indicate a combination of a metal atom, in this case a rhodium atom, with one or more electronicallyrich "ligand" molecules or atoms capable of independent existence. Conversely, the "ligand" has a pair of electrons capable of bonding with the metal atom and forming the complex. The term "immobilized" as used in describing the invention refers to the action of chemical or physical forces which prevent the rhodium complexes in solution in the polar solution of the catalyst from migrating into the organic reactant phase.

For immobilization of the aqueous solution of the organometallic complex, the solid surface is necessarily specified as a hydrophilic surface which is effectively wetted by the aqueous solution. Many of the ligands preferred for forming water soluble rhodium complexes are surface active and promote such wetting. In addition, the solid must be one which retains its structural integrity in the presence of water. Suitable solid surfaces are exemplified by silicas, aluminas, titanias, aluminophosphates, carbon, organic polymers, and compacted clays.

Although not in principle necessary to the catalyst of this invention, a porous solid is preferred in order to provide greater surface area for interface of the immobilized aqueous film with the separate and distinct bulk reactant phase. It has further been observed that, with porous supports having a broad distribution in pore sizes, the aqueous solution of the catalyst does not distribute uniformly over the surface but instead preferentially distributes into the smaller pores. As a result, the aqueous phase may block access of the organic reactant into these smaller pores, while the surfaces of the larger pores are incompletely loaded with the aqueous phase. For such reasons, a solid porous support characterized by pores of relatively uniform size is more preferred. Examples of narrow pore size distribution supports include high silica glasses, which are commercially available with mean pore diameters in the range from about 70 to 3,000Å. Preferably, the pores of a porous support are predominantly of a diameter greater than about 20Å.

Immobilized on the solid surface, in the form of a film of an aqueous solution, is at least one rhodium complex having catalytic activity, for instance in hydroformylation, hydrogenation, isomerization or other reaction(s). The complex and the ligand from which it is formed are necessarily soluble in a catalytically effective amount in water. Moreover, the ligand and the organometallic complex are preferentially soluble in the aqueous phase of the supported catalyst, relative to their solubility in the organic reactant phase, and are preferably essentially insoluble in the organic reactant phase.

Water-soluble ligands and rhodium complexes thereof are known in the art. One class of very suitable complexes is formed from ligands (e.g., tertiary phosphine or phosphite ligands) wherein the molecule contains one or more organic moieties (e.g., alkyl or aryl groups) which have been "functionalized" by addition of one or more substituents (e.g., one or more carbonyl, carboxyl, nitro, amino, hydroxy, sulfonate, sulfate, phosphate, ether, polyether, or quaternary ammonium groups) to aid in their solubilization in aqueous solution. Specific members of this class are exemplified by the water soluble sulfonated phosphine ligands and rhodium complexes thereof, as described in U.S. Pat. No. 4,248,802. The disclosures of this patent relative to such ligands and their rhodium complexes are incorporated herein by this reference.

Particularly described in U.S. Pat. No. 4,248,802 are rhodium complexes of at least one water soluble phosphine having the formula

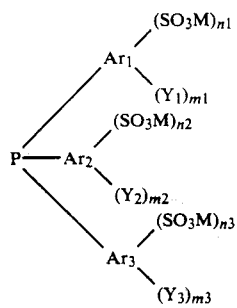

in which:

$Ar_1$, $Ar_2$ and $Ar_3$, which may be identical or different, represent aryl groups having from 6 to 10 carbon atoms, $Y_1$, $Y_2$ and $Y_3$, which may be identical or different, each represents a radical selected from the group consisting of linear or branched chain alkyl radicals having from 1 to 4 carbon atoms, alkoxy radicals having from m1 to 4 carbon atoms, halogen atoms, the —OH radical, the —C≡N radical, the —NO$_2$ radical and the radical of the formula —NR$_1$R$_2$, in which R$_1$ and R$_2$, which may be identical or different, represent a linear or branched chain alkyl radical having from 1 to 4 carbon atoms, M is an inorganic or organic cationic radical selected from the group consisting of the cations derived from the alkali metals, the alkaline earth metals, lead, zinc and copper, $NH_4^+$, and $N(R_3R_4R_5R_6)^{30}$ wherein $R_3$, $R_4$, $R_5$ and $R_6$, which may be identical or different, each represents a linear or branched chain alkyl radical having from 1 to 4 carbon atoms, m1, m2 and m3 are identical or different integers between 0 and 5 and n1, n2 and n3 are identical or different integers between 0 and 3, at least one of the numbers n1, n2 or n3 being greater than or equal to 1.

While the concentration of the rhodium complex in the immobilized polar solution of the catalyst is not critical to the invention, a solution having a relatively high concentration of the complex is desirable from the standpoint of higher catalyst activity. Moreover, the complex is often more stable in more concentrated solutions. A catalyst containing a quantity of immobilized rhodium complex which is greater than the limit of the solubility of the complex in the available water (that is, a catalyst containing the complex both in solution in aqueous phase and also as a separate undissolved component immobilized on the solid) is very suitable. In any event, however, the catalyst must contain an activating amount of water, that is, an amount which is equal to or greater than that corresponding to the water of hydration of the complex. The presence of water in at least an activating amount results in an increase in catalytic activity, relative to the activity of catalysts which do not comprise a distinct aqueous solution immobilized on the solid. Typically, the catalyst is suitably activated by the presence in the immobilized catalyst solution of a quantity of water which is about ten percent or more by weight, relative to the quantity of the rhodium complex present.

This invention further extends to one preferred method for making catalysts of this invention. Under this method, the solid surface is initially impregnated with the organometallic complex, followed by addition of sufficient water to dissolve all or part of the complex, thereby forming an aqueous solution which coats, in whole or part the available solid surface area. For the initial impregnation, the complex can, for instance, be introduced into the pores of a porous solid as a solution in any convenient solvent. Removal of this solvent by evaporation under relatively mild conditions, and preferably under vacuum, deposits the rhodium complex over the external and pore surfaces. Water for the final complex solution can then be added in a controlled manner, for instance, as vapor which condenses on the surface and dissolves (in whole or part) the complex. This two step approach to immobilization of the complex solution on the solid surface, has advantage over a one step process alternative, in which the solid is coated directly with the aqueous organometallic complex solution. In a one step impregnation and immobilization, it is often difficult to control the uniformity of the distribution of the solution over the solid surface, particularly over the surface of a porous solid. Uneven distribution of the liquid solution in the porous solid decreases the effective interfacial area between the aqueous catalyst solution and an organic reactant phase.

If an aqueous solution is used to impregnate the solid with the rhodium complex, a catalyst characterized by a relatively uniform distribution of the catalytic solution can also be obtained by controlled drying, leaving an activating amount of water in the solution.

In any preparation of the catalyst of the invention, the loading of aqueous solution onto the solid surface (or, equivalently, the formation of the solution on the solid surface) is preferably relatively uniform. Filling or blocking of the pores of a porous solid catalyst component should be avoided, as it decreases interfacial surface area between the immobilized aqueous solution and the organic reactant phase, and can lower catalyst activity.

Without intention that the catalyst of the invention be limited in its applications to one theory or mechanism of operation, it is thought that the aqueous complex solution catalyzes reactions at the interface between the two essentially immiscible phases: (1) the organic reactant phase and (2) the supported aqueous phase of the catalyst. A catalyst according to the invention, having an aqueous phase supported on the surface of a solid, provides an interfacial area between an organic reactant and the aqueous phase which is significantly increased over that which could be reasonably expected from simple agitation of two immiscible liquids.

By virtue of its heterogeneous, solid character, the specified catalyst is readily applied in a stirred tank or fixed or fluid bed reactor, and to either a batch or continuous mode of operation. In other respects, the process of the invention is suitably carried out using procedures and equipment conventionally applied to reaction processes catalyzed by organometallic complexes, particularly rhodium complexes. Following its application in an organic liquid reaction mixture, the heterogeneous catalyst of the invention is readily removed from the product by gravity settling, centrifugation, filtration and/or one or more other solid-liquid separation techniques. The organic product mixture is recovered and treated, as desired, for product separation and purification, reactant separation and recycle, etc.

The invention is further described with reference to the following examples, which illustrate certain preferred embodiments of the invention and are not intended to limit its broader scope. The examples further illustrate application of the catalyst of the invention to the catalysis of various liquid phase reactions.

EXAMPLE 1

Catalyst preparation

A supported aqueous phase catalyst according to the invention was prepared, in which the solid support was a controlled pore glass CPG-240 (obtained from Electro-Nucleonics, Inc., and characterized by a 120/200 mesh size, a mean pore diameter of 237A±4.3%, a pore volume of 0.95 ml/g, and a surface area of 77.5 m$^2$/g) and the organometallic complex was hydridocarbonyl tris(sodiumtriphenylphosphine trisulfonate) rhodium(I).

Triphenylphosphine trisulfonate was first synthesized by the following procedures. Triphenylphosphine, 8 grams, was vacuum deaerated, blanketed with argon, and cooled to 10° C in a water bath. Then, 13.7 ml of sulfuric acid (95%) were added dropwise with vigorous stirring. (Unless otherwise indicated, concentrations noted herein are given in percent by weight.) Stirring was continued until complete dissolution. A mixture of 10.8 ml of 30% sulfur trioxide in sulfuric acid and 16.6 ml of 99% sulfur trioxide was added slowly dropwise with stirring. The temperature of the water bath was allowed to increase to 20.5° C over a seven-hour period. After twelve hours, the reaction was quenched by cooling to 6° C, followed by the dropwise addition of 200 ml deareated cooled water. The resulting aqueous solution was extracted two times with 50 grams each of tributylphosphate. The tributylphosphate layer was neutralized by vigorous stirring with 50% sodium hydroxide in water in an ice bath with agitation under an argon atmosphere. The resultant sludge was washed five times with 100 ml of ethyl ether per washing and then vacuum dried. The sludge was then dissolved in 75 ml of distilled water. Addition of 75 ml absolute methanol generated a brown precipitate, which was removed by filtration. The mother liquor was evaporated under vacuum to give high purity sodium triphenylphosphine tri-metasulfonate. Yield was 29%, calculated on triphenylphosphine starting material.

Hydridocarbonyl tris(sodiumtriphenylphosphine trisulfonate) rhodium(I) was then prepared from the triphenylphosphine trisulfonate. For this purpose, 50 milligrams (mg) of acetylacetonate dicarbonyl rhodium(I) were added to a vigorously stirred one ml deaerated solution of 400 mg of the sodium triphenylphosphine trisulfonate in water. After complete dissolution, stirring was continued for six hours under an atmosphere of hydrogen and carbon monoxide (a 1:1 molar ratio of H2 to CO) at room temperature and atmospheric pressure. The resulting solution was filtered under nitrogen to remove small amounts of rhodium metal present. Then 8 ml of absolute ethanol saturated with a mixture of H$_2$/CO (1:1 by mol) were added to precipitate the desired complex. The mixture was centrifuged to recover the precipitate, which was then washed with absolute ethanol and vacuum dried. Analysis indicated a high purity hydridocarbonyl tris(sodiumtriphenylphosphine trisulfonate) rhodium(I) complex, with no detectable phosphine oxide.

This complex was next immobilized on the solid catalyst support. The solid complex was dissolved in 25 ml of deaerated water, along with 410 mg of triphenylphosphine trisulfonate, and the resulting solution was poured into 8.8 grams of the CPG-240 solid, which had been previously deaerated and argon blanketed. The slurry obtained was degassed under vacuum and blanketed with argon at one atmosphere. Finally, the slurry was dried under vacuum to a water content of about 2.9%w, based on the weight of the dry solid (or, equivalently, about 2.8%w based on total catalyst weight. The resulting material was stored at atmospheric pressure and room temperature under an atmosphere of H$_2$ and CO (1:1 mol).

EXAMPLE 2

Water addition

A twenty milligram quantity of the catalyst from Example 1 was loaded into a microreactor immersed in a thermostatic bath at 30° C. After evacuation under vacuum, the catalyst was allowed to adsorb water. Communication was established between the reactor and the vapor space of a flask of degassed water, which was also immersed in the 30° C thermostatic bath. After ninety minutes of exposure to the water vapor, argon was admitted into the system and the reactor was closed.

The hydrated catalyst of Example 2 contained about 8.5%w of water calculated on the weight of the dry solid (about 7.5%w calculated on total weight of the catalyst).

EXAMPLE 3

Hydroformylation of oleyl alcohol

The catalyst prepared as described in Example 1 was applied to the hydroformylation of oleyl alcohol, under the following procedures.

Under a dry nitrogen atmosphere, the microreactor was loaded with 0.10 grams of the catalyst prepared in Example 1 and 0.10 grams of oleyl alcohol (in a 25% by volume solution in cyclohexane). The reactor was then flushed with a $H_2/CO$ mixture (1:1 by mol) and pressurized with the same $H_2/CO$ mixture to 825 psig. The reactor was heated to 100° C and maintained at that temperature with stirring for 5.5 hours. Analysis of the product showed a conversion of 96.6% of the oleyl alcohol and confirmed that the double bond of the alcohol had undergone hydroformylation.

EXAMPLE 4

Evaluation of rhodium leaching

The slurry of reactants, products and catalyst in the reactor at the completion of the hydroformylation reaction of Example 3 was filtered to separate out the supported catalyst particles. To the filtered liquid was added sufficient additional oleyl alcohol to raise its concentration from 3.4% to 46%. For a period of nine hours, the resulting solution was then subjected to the same temperature, $H_2/CO$ pressure and stirring conditions as the hydroformylation reaction mixture of Example 3. No increase in the concentration of aldehydes was observed.

To further evaluate the possibility of the loss of rhodium from the catalyst during the reaction of Example 3, the cyclohexane solvent was evaporated from the solution. To the oleyl alcohol reactant and its hydroformylation products remaining after the evaporation of the cyclohexane, 0.10 ml of 1-hexene was added. The reactor was flushed with hydrogen and pressurized at 60 psig with hydrogen. The temperature was raised to 100° C and the reactor contents stirred under hydrogen for 2 hours. No hydrogenation of the 1-hexene was detected, indicating no zero valent rhodium metal in the system.

These experiments indicate that the catalytically active rhodium complex remains effectively immobilized on the solid surface of the catalyst during the hydroformylation process of this invention.

EXAMPLES 5-8

A series of other catalysts according to the invention, were prepared following the procedures of Examples 1 and 2, but varying the duration of their exposure to water vapor during hydration of the impregnated support and, thus, the quantity of water in the aqueous phase of the finished catalyst. The parameters for the hydration step in the preparation of each of the catalysts of Examples 1, 2, and 5–8 are shown in the following Table. Water content of the finished catalyst is given in terms of percent by weight (%w) of water, relative to weight of the total catalyst.

| Example No. | Duration of Exposure to Water Vapor (Hours) | Water Content of Finished Catalyst (% w) |
| --- | --- | --- |
| 1 | 0 | 2.8 |
| 5 | 0.75 | — |
| 2 | 1.5 | 7.5 |
| 6 | 3 | — |
| 7 | 6 | 31 |
| 8 | 6.5 | — |

EXAMPLES 9-14

Hydroformylation of 1-octene

In Examples 9–14, each of the supported aqueous phase catalysts prepared as described in Examples 1, 5, 2 and 6–8, respectively, was evaluated as a catalyst for the hydroformylation of 1-octene.

For each of the hydroformylation reactions, 0.40 ml of a solution of 1-octene (20% by volume in degassed cyclohexane) was introduced into the microreactor containing the finished catalyst. The reactor was flushed with a $H_2/CO$ mixture (1:1 mol), pressurized with 750 psig of this $H_2/CO$ mixture and stirred in an oil bath at 70° C. After five hours, the reaction was stopped and the product mixture analyzed to determine the conversion of 1-octene to $C_9$ aldehyde, and the ratio of linear to branched carbon chain $C_9$ aldehydes. Results of the hydroformylation reactions are summarized in the following table.

| Example No. | Applying Catalyst of Example No. | Octene Conversion (%) | Ratio of Linear to Branched Aldehydes |
| --- | --- | --- | --- |
| 9 | 1 | 10 | 2.1 |
| 10 | 5 | 38.5 | 2.9 |
| 11 | 2 | 62.5 | 2.7 |
| 12 | 6 | 45 | 2.85 |
| 13 | 7 | 5.9 | 2.5 |
| 14 | 8 | 4.1 | 2.5 |

EXAMPLES 15-18

In a manner similar to that described in Example 9, other olefinically-unsaturated reactant compounds were hydroformulated in the presence of the catalyst described in Example 1. The olefinic reactant was introduced as a 20% by volume solution in cyclohexane in Example 15, and as a 50% by volume solution in Examples 16, 17 and 18. Other reaction conditions and the results for each of these examples are summarized in the following Table.

| Example No. | Olefinically Unsaturated Reactant | Grams Rh Per Gram Reactant | $H_2/CO$ Pressure (psig) | Temperature (°C.) |
| --- | --- | --- | --- | --- |
| 15 | 1-octene | 0.001 | 725 | 95 |
| 16 | c-jasmone | 0.0002 | 750 | 100 |
| 17 | dicyclopentadiene | 0.0002 | 750 | 100 |
| 18 | dicyclopentadiene | 0.0002 | 750 | 100 |

| Example No. | Reaction Time (Hours) | Conversion (%) | Comments |
| --- | --- | --- | --- |
| 15 | 3 | 98.7 | normal/branched ratio = 1.8 |
| 16 | 5 | 86.5 | 38% dialdehydes |
| 17 | 5 | 74.4 | 0.7% dialdehydes |
| 18 | 10 | 100 | 9.2% dialdehydes |

We claim as our invention:

1. A catalyst comprising a porous solid having immobilized on the external and pore surfaces thereof an aqueous solution of one or more organometallic complexes of rhodium.

2. The catalyst of claim 1, wherein the aqueous solution is immobilized on the external and pore surfaces of a porous solid, the pores of which are predominantly of diameter greater than about 20Å.

3. The catalyst of claim 2, wherein the catalyst comprises a solid surface having immobilized thereon an aqueous solution of one or more sulfonated phosphine complexes of rhodium.

4. The catalyst of claim 3, wherein one or more of the sulfonated phosphine complexes of are tri-sulfonated complexes.

5. The catalyst of any one of claims 1 through 4, wherein the aqueous solution of the catalyst contains a quantity of water which is at least equal to that corresponding to the water of hydration of the one or more rhodium complexes.

6. The catalyst of claim 5, wherein the catalyst solution comprises a quantity of water which is at least about ten percent by weight, relative to the quantity of the one or more rhodium complexes present.

7. A process for the preparation of supported aqueous phase catalysts, which comprises steps for impregnating the external and pore surfaces of a porous solid catalyst support with a solution of at least one water soluble organometallic complex of rhodium in a volatile solvent, evaporating said solvent from the impregnated catalyst, and condensing water vapor on the surfaces of the solid to form on said surfaces a film of an aqueous solution of the rhodium complex.

8. The catalyst of claim 2, wherein the pores of the porous solid have a mean pore diameter in the range from about 70 to 3,000Å.

9. The catalyst of claim 6, wherein the pores of the porous solid have a mean pore diameter in the range from about 70 to 3,000Å.

10. The catalyst of claim 8, wherein the porous solid is a silica.

11. The catalyst of claim 9, wherein the porous solid is a silica.

12. The catalyst of claim 8, wherein the porous solid is a glass.

13. The catalyst of claim 9, wherein the porous solid is a glass.

14. The catalyst of claim 3, wherein the sulfonated phosphine complex is a complex of at least one water soluble phosphine having the formula

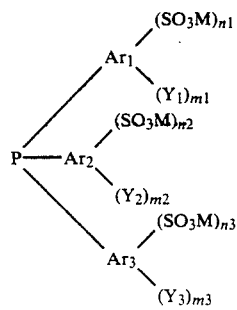

in which:

Ar$_1$, Ar$_2$ and Ar$_3$, which may be identical or different, represent aryl groups having from 6 to 10 carbon atoms, Y$_1$, Y$_2$ and Y$_3$, which may be identical or different, each represents a radical selected from the group consisting of linear or branched chain alkyl radicals having from 1 to 4 carbon atoms, alkoxy radicals having from 1 to 4 carbon atoms, halogen atoms, the —OH radical, the —C≡N radical, the —NO$_2$ radical and the radical of the formula —NR$_1$R$_2$, in which R$_1$ and R$_2$, which may be identical or different, represent a linear or branched chain alkyl radical having from 1 to 4 carbon atoms, M is an inorganic or organic cationic radical selected from the group consisting of the cations derived from the alkali metals, the alkaline earth metals, lead, zinc and copper, NH$_4^+$, and N(R$_3$R$_4$R$_5$R$_6$)$^+$ wherein R$_3$, R$_4$, R$_5$ and R$_6$, which may be identical or different, each represents a linear or branched chain alkyl radical having from 1 to 4 carbon atoms, m1, m2 and m3 are identical or different integers between 0 and 5 and n1, n2 and n3 are identical or different integers between 0 and 3, at least one of the numbers n1, n2 or n3 being greater than or equal to 1.

15. The catalyst of claim 14, wherein the pores of the porous solid have a mean pore diameter in the range from about 70 to 3,000Å, and the complex is a tri-sulfonated complex.

16. The process of claim 7, wherein the process further comprises condensing sufficient water vapor on the surfaces of the solid to form a film of aqueous solution comprising a quantity of water which is at least about ten percent by weight, relative to the quantity of the one or more rhodium complexes present.

17. The process of either claim 7 or claim 16, wherein the pores of the porous solid are predominantly of diameter greater than about 20Å.

18. The process of claim 17, wherein the pores of the porous solid have a mean pore diameter in the range from about 70 to 3,000Å.

19. The process of claim 18, wherein at least one of the rhodium complexes is a sulfonated phosphine complex of rhodium.

20. The process of claim 19, wherein the sulfonated phosphine complex is a complex of at least one water soluble phosphine having the formula described in claim 14.

21. The process of claim 18, wherein the porous solid is a silica.

22. The process of claim 18, wherein the porous solid is a glass.

23. The process of claim 21, wherein at least one of the rhodium complexes is a tri-sulfonated phosphine complex of rhodium which is a complex of at least one water soluble phosphine having the formula

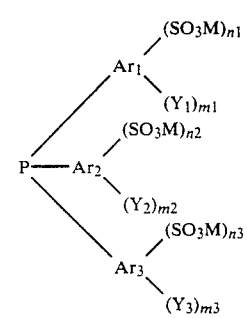

in which:

Ar$_1$, Ar$_2$ and Ar$_3$, which may be identical or different, represent aryl groups having from 6 to 10 carbon atoms, Y$_1$, Y$_2$ and Y$_3$, which may be identical or different, each represents a radical selected from the group consisting of linear or branched chain alkyl radicals having from 1 to 4 carbon atoms, alkoxy radicals having from 1 to 4 carbon atoms, halogen atoms, the —OH radical, the —C=N radical, the —NO$_2$ radical and the radical of the formula —NR$_2$R$_2$, in which R$_1$ and R$_2$, which may be identical or different, represent a linear or branched chain alkyl radical having from 1 to 4 carbon atoms, M is an inorganic or organic cationic radical selected from the group consisting of the cations derived from the alkali metals, the alkaline earth metals, lead, zinc and copper, NH$_4^+$, and N(R$_3$R$_4$R$_5$R$_6$)= wherein R$_3$, R$_4$, R$_5$ and R$_6$, which may be identical or different, each represents a linear or branched chain alkyl radical having from 1 to 4 carbon atoms, m1, m2 and m3 are identical or different integers between 0 and 5 and n1, n2 and n3 are identical or different integers between 0 and 3, at least one of the numbers n1, n2 or n3 being greater than or equal to 1.

24. The process of claim 22, wherein at least one of the rhodium complexes is a tri-sulfonated phosphine complex of rhodium which is a complex of at least one water soluble phosphine having the formula

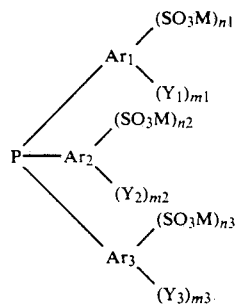

in which:

Ar$_1$, Ar$_2$ and Ar$_3$, which may be identical or different, represent aryl groups having from 6 to 10 carbon atoms, Y$_1$, Y$_2$ and Y$_3$, which may be identical or different, each represents a radical selected from the group consisting of linear or branched chain alkyl radicals having from 1 to 4 carbon atoms, alkoxy radicals having from 1 to 4 carbon atoms, halogen atoms, the —OH radical, the —C=N radical, the —NO$_2$ radical the radical of the formula —NR$_1$R$_2$, in which R$_1$ and R$_2$, which may be identical or different, represent a linear or branched chain alkyl radical having from 1 to 4 carbon atoms, M is an inorganic or organic cationic radical selected from the group consisting of the cations derived from the alkali metals, the alkaline earth metals, lead, zinc and copper, NH$_4$=, and N(R$_3$R$_4$R$_5$R$_6$)= wherein R$_3$, R$_4$, R$_5$ and R$_6$, which may be identical or different, each represents a linear or branched chain alkyl radical having from 1 to 4 carbon atoms, m1, m2 and m3 are identical or different integers between 0 and 5 and n1, n2 and n3 are identical or different integers between 0 and 3, at least one of the numbers n1, n2 or n3 being greater than or equal to 1.

* * * * *